(12) United States Patent
Ogata et al.

(10) Patent No.: US 7,456,321 B2
(45) Date of Patent: Nov. 25, 2008

(54) PROCESS FOR PRODUCING HIGH-PURITY 4,4'-DIHYDROXYDIPHENYL SULFONE

(75) Inventors: Eiji Ogata, Wakayama (JP); Fumio Oi, Wakayama (JP); Norio Yanase, Wakayama (JP); Nobuyuki Nate, Wakayama (JP)

(73) Assignee: Konishi Chemical Ind. Co., Ltd., Wakayama-shi, Wakayama (JP)

( * ) Notice: Subject to any disclaimer, the term of this patent is extended or adjusted under 35 U.S.C. 154(b) by 564 days.

(21) Appl. No.: 10/529,074

(22) PCT Filed: Sep. 22, 2003

(86) PCT No.: PCT/JP03/12049

§ 371 (c)(1), (2), (4) Date: Mar. 24, 2005

(87) PCT Pub. No.: WO2004/029020

PCT Pub. Date: Apr. 8, 2004

(65) Prior Publication Data

US 2005/0272956 A1 Dec. 8, 2005

(30) Foreign Application Priority Data

Sep. 25, 2002 (JP) .............................. 2002-279199

(51) Int. Cl.
*C07F 315/00* (2006.01)
(52) U.S. Cl. ....................................................... 568/34
(58) Field of Classification Search ................... 568/34, 568/33
See application file for complete search history.

(56) References Cited

U.S. PATENT DOCUMENTS

| 4,820,831 A | * | 4/1989 | Ogata et al. ................ 568/33 |
| 5,041,677 A | | 8/1991 | Cooker et al. |
| 5,189,223 A | * | 2/1993 | Ogata et al. ................ 568/33 |
| 5,241,121 A | * | 8/1993 | Ogata et al. ................ 568/33 |
| 6,700,020 B2 | * | 3/2004 | Pabst et al. ................ 568/33 |

FOREIGN PATENT DOCUMENTS

| EP | 0 443 046 A1 | | 8/1991 |
| JP | 51-036264 B | | 10/1976 |
| JP | 63048261 | * | 2/1988 |
| JP | 04-145061 A | | 5/1992 |
| JP | 04145061 | * | 5/1992 |
| JP | 04-074347 B | | 11/1992 |
| JP | 07-091261 B | | 10/1995 |
| JP | 08-002861 B | | 1/1996 |
| JP | 08-002863 B | | 1/1996 |
| WO | WO 92/02493 | * | 2/1992 |

* cited by examiner

*Primary Examiner*—Yvonne Eyler
*Assistant Examiner*—Chukwuma O Nwaonicha
(74) *Attorney, Agent, or Firm*—Knobbe Martens Olson & Bear LLP

(57) ABSTRACT

The present invention provides a process for producing 4,4'-dihydroxydiphenylsulfone of very high purity. In particular, the present invention provides a process for producing 4,4'-dihydroxydiphenylsulfone of high purity comprising the steps of subjecting phenol in combination with a sulfonating agent or phenolsulfonic acid to a dehydration reaction in the presence of an aromatic nonpolar solvent while suspending the resulting dihydroxydiphenylsulfone therein, mixing the reaction suspension with a polar solvent to at least partially dissolve the dihydroxydiphenylsulfone, and precipitating 4,4'-dihydroxydiphenylsulfone.

13 Claims, No Drawings

PROCESS FOR PRODUCING HIGH-PURITY 4,4'-DIHYDROXYDIPHENYL SULFONE

This application is the U.S. National Phase under 35 U.S.C. §371 of International Application PCT/JP2003/012049, filed Sep. 22, 2003, which claims priority to Japanese Patent Application No. 2002-279199, filed Sep. 25, 2002. The International Applicatiion was not published under PCT Article 21(2) in English.

TECHNICAL FIELD

The present invention relates to a process for producing 4,4'-dihydroxydiphenylsulfone (hereinafter sometimes referred to as "4,4'-BS") of high purity.

BACKGROUND ART 4,4'-BS is an important compound in the fields of chemical industry involving textiles, resins, etc. Recently, 4,4'-BS of higher purity is required in these fields.

A method that has been employed is a "method for isolating 4,4'-BS from a dihydroxydiphenylsulfone isomeric mixture comprising treating a dihydroxydiphenylsulfone isomeric mixture with a mixed solvent composed of 80-40 wt. % of o-dichlorobenzene and 20-60 wt. % of phenol, and filtering off the resulting product without heating to isolate 4,4'-BS" (Japanese Patent Publication No. 1976-36264).

However this method does not give 4,4'-BS in high yields.

Another method that has been employed is a "method for synthesizing 4,4'-BS comprising reacting phenol with sulfuric acid in an inert solvent having a weight about 15 to about 35% of the weight of the reactants to produce an isomeric mixture, removing water from the reaction system at about 160 to about 200° C. by heating, maintaining the temperature of the resulting reaction mixture at about 160 to about 200° C. until the generation of water terminates, cooling the water-removed reaction mixture to about 80 to about 120° C., adding if necessary a replenishing amount of the inert solvent, forming a slurry in which the weight of the inert solvent accounts for about 20 to about 80% of the reaction mixture, and separating the slurry into crystalline 4,4'-BS and a liquid in which 2,4'-BS is dissolved (see Japanese Patent Publication No. 1992-74347).

According to Japanese Patent Publication No. 1992-74347, 4,4'-BS can be obtained with purities of 93.5 wt. % (Example 1) and 95.3 wt. % (Example 2). Japanese Patent Publication No. 1992-74347 does not disclose a method that can produce 4,4'-BS of higher purity. Moreover, although the examples in Patent Publication 2 recite that "by-products were not detected by gas chromatography", phenolsulfonic acid undetectable by gas chromatography often remains as an impurity.

DISCLOSURE OF THE INVENTION

An object of the present invention is to provide a process for producing dihydroxydiphenylsulfone wherein trihydroxytriphenyldisulfone (TTDS) and coloring impurities are effectively removed without altering the isomeric composition of dihydroxydiphenylsulfone.

The inventors conducted extensive research and found that the object described above can be achieved by subjecting phenol in combination with a sulfonating agent or phenolsulfonic acid to a dehydration reaction in the presence of an aromatic nonpolar solvent while suspending the resulting dihydroxydiphenylsulfone therein, mixing the reaction suspension with a polar solvent to at least partially dissolve the dihydroxydiphenylsulfone, and precipitating the dihydroxydiphenylsulfone. The inventors thereby accomplished the invention.

In other words, the present invention relates to processes for producing 4,4'-BS as presented below:

1. A process for producing 4,4'-dihydroxydiphenylsulfone of high purity comprising the steps of:
   subjecting phenol in combination with a sulfonating agent or phenolsulfonic acid to a dehydration reaction in the presence of an aromatic nonpolar solvent while suspending the resulting dihydroxydiphenylsulfone therein;
   mixing the resulting reaction suspension with a polar solvent to at least partially dissolve the dihydroxydiphenylsulfone; and
   precipitating dissolved 4,4'-dihydroxydiphenylsulfone.
2. A process for producing 4,4'-dihydroxydiphenylsulfone of high purity comprising the steps of:
   subjecting phenol in combination with a sulfonating agent or phenolsulfonic acid to a dehydration reaction in the presence of an aromatic nonpolar solvent while suspending the resulting dihydroxydiphenylsulfone therein;
   mixing the resulting reaction suspension with a polar solvent to at least partially dissolve the dihydroxydiphenylsulfone;
   primarily precipitating dissolved 4,4'-dihydroxydiphenylsulfone;
   isolating the resulting 4,4'-dihydroxydiphenylsulfone by filtration or decantation;
   distilling off the solvents contained in the liquid obtained after the isolation of the 4,4'-dihydroxydiphenylsulfone to produce a suspension or distillation residue;
   at least partially dissolving solids contained in the suspension or the residue in a mixed solvent of a polar solvent and a nonpolar solvent; and
   secondarily precipitating 4,4'-dihydroxydiphenylsulfone.
3. A process for producing 4,4'-dihydroxydiphenylsulfone of high purity according to Item 1 or 2, wherein the dehydration reaction between phenol and a sulfonating agent or phenolsulfonic acid is carried out in the presence of an acid catalyst.
4. A process for producing 4,4'-dihydroxydiphenylsulfone of high purity according to any one of Items 1 to 3, wherein the aromatic nonpolar solvent is mesitylene.
5. A process for producing 4,4'-dihydroxydiphenylsulfone of high purity according to any one of Items 1 to 4, wherein the polar solvent is selected from the group consisting of $C_{4-15}$ higher alcohols, polyols, and phenols.
6. A process for producing 4,4'-dihydroxydiphenylsulfone of high purity according to any one of Items 1 to 5, wherein the polar solvent is phenol.
7. A process for producing 4,4'-dihydroxydiphenylsulfone of high purity according to any one of Items 1 to 6, wherein the reaction suspension and the polar solvent are mixed while heating under pressure to at least partially dissolve dihydroxydiphenylsulfone.
8. A process for producing 4,4'-dihydroxydiphenylsulfone of high purity according to any one of Items 2 to 7, wherein the solids contained in the suspension or the residue is at least partially dissolved in a mixed solvent of a polar solvent and a nonpolar solvent while heating under pressure.
9. A process for producing 4,4'-dihydroxydiphenylsulfone of high purity according to any one of Items 2 to 8, wherein before or after the dehydration reaction between phenol and a sulfonating agent or phenolsulfonic acid, 4,4'-dihydroxydiphenylsulfone obtained by secondary precipitation is introduced into the reaction system.

10. A process for producing 4,4'-dihydroxydiphenylsulfone of high purity according to Item 2, wherein the temperature is maintained at the isomerization temperature or higher even after the solvents contained in the liquid obtained after the isolation of the primarily precipitated 4,4'-dihydroxydiphenylsulfone by filtration or decantation are distilled off to produce a suspension or distillation residue.

In the present invention, phenol in combination with a sulfonating agent or phenolsulfonic acid is subjected to a dehydration reaction in the presence of an aromatic nonpolar solvent. This dehydration reaction is proceeded while suspending the resulting dihydroxydiphenylsulfone. The dihydroxydiphenylsulfone (hereinafter sometimes referred to as "BS") generated by the dehydration reaction is an isomeric mixture of 2,4'-BS and 4,4'-BS, with 2,4'-BS being contained in a small amount.

Known sulfonating agents are usable in the dehydration reaction, for example, concentrated sulfuric acid, sulfuric anhydride, fuming sulfuric acid, chlorosulfonic acid, etc.

Although the ratio of sulfonating agent or phenolsulfonic acid relative to phenol is not limited and can be suitably selected from a broad range, it is usually stoichiometric or in the proximity thereof. More specifically, the molar ratio of phenol is about 1.9 to about 2.1 mol per mol of sulfonating agent, and about 0.9 to about 1.1 mol per mol of phenolsulfonic acid. Ratios within the aforementioned ranges enhance the production of 4,4'-BS of high purity in high yields.

An aromatic nonpolar solvent is used in the dehydration reaction as a reaction medium. Preferable reaction media do not substantially dissolve 4,4'-BS.

Examples of aromatic nonpolar solvents are chlorobenzene (boiling point: 132° C.), dichlorobenzene (boiling point: 180° C.), trichlorobenzene (boiling point: 212° C.), chlorotoluene (boiling point: 162° C.), 3,4-dichlorotoluene (boiling point: 209° C.), diethylbenzene (boiling point: 182° C.), mesitylene (boiling point: 165° C.), tetralin (boiling point: 207° C.), etc. Aromatic nonpolar solvents can be used singly or as a combination of two or more species.

Aromatic nonpolar solvents may be used in combination with other nonpolar solvents such as aliphatic hydrocarbon solvents. When used in combination with other nonpolar solvents, aromatic nonpolar solvents are used usually in a proportion of about 50 wt. % or greater, and preferably about 70 wt. % or greater, of the entire reaction medium. Hereinafter, aromatic nonpolar solvents, and mixed solvents of aromatic nonpolar solvents and other nonpolar solvents, are sometimes referred to as the "reaction medium".

Examples of aliphatic hydrocarbon solvents are linear aliphatic hydrocarbons such as n-decane; branched hydrocarbons such as Isopar G and Isopar H manufactured by Exxon Mobile Corporation; alicyclic hydrocarbons such as decalins (boiling point of trans-decalin: 185.5° C., boiling point of cis-decalin: 195.7° C.); halogenated aliphatic hydrocarbons such as tetrachloroethane (boiling point: 146° C.); etc. Aliphatic hydrocarbon solvents may be used singly or as a combination of two or more species.

Mesitylene, chlorotoluene, 3,4-dichlorotoluene, diethylbenzene, etc., are preferable as aromatic nonpolar solvents. Mesitylene is particularly preferable. The use of mesitylene enables the reaction system to be easily stirred, the resultant BS to be stably precipitated as fine particles, and the temperature of the reaction system to be easily controlled, and therefore mesitylene is preferable. Moreover, the use of mesitylene is preferable for producing 4,4'-BS of high purity in high yields.

Although the amount of reaction medium is not limited insofar as it is sufficient for stirring the reaction fluid, the weight ratio of reaction medium to theoretical yield of dihydroxydiphenylsulfone is usually about 1 to 0.1-5, and preferably about 1 to 0.2-3. When aromatic nonpolar solvents are used in combination with other nonpolar solvents such as aliphatic hydrocarbon solvents, the total weight of aromatic nonpolar solvents and other nonpolar solvents is regarded as the weight of reaction medium.

It is preferable to carry out the dehydration reaction while removing from the reaction system the water generated therein. For example, the reaction is carried out while distilling off water in conjunction with the reaction medium containing, e.g, aromatic nonpolar solvents and aliphatic hydrocarbon solvents. After the removal of water, the reaction medium containing, e.g, aromatic nonpolar solvents and aliphatic hydrocarbon solvents, may be returned to the reaction system.

Reaction conditions such as temperature, pressure, reaction time, etc., for the dehydration reaction, can be suitably selected by reference to known methods. For example, conditions selected for methods described in Japanese Patent Publication Nos. 1995-91261, 1996-2861, 1996-2863, etc., are applicable herein.

The reaction temperature for the dehydration reaction is usually about 120° C. or higher, preferably about 120 to about 220° C., and more preferably about 140 to 190° C. Although the dehydration reaction proceeds at ordinary pressures, it can be carried out under pressure or under reduced pressure as necessary. The reaction time is not limited and can be suitably selected according to the reaction temperature and other factors, but it is usually about 1 to 30 hours, and preferably about 2 to about 20 hours.

In the process of the invention, the temperature after the dehydration reaction may be maintained at the isomerization temperature or higher while suspending the dihydroxydiphenylsulfone. The isomerization from 2,4'-BS to 4,4'-BS is enhanced by maintaining the temperature at the isomerization temperature or higher.

Although the temperature level to be maintained is not limited insofar as the isomerization from 2,4'-BS to 4,4'-BS proceeds, it is usually about 120° C. or higher and preferably about 140 to 175° C. Temperatures within the aforementioned ranges allow prompt isomerization. Although the period for maintaining a temperature at the isomerization temperature or higher after the dehydration reaction can be suitably selected according to the reaction temperature and other factors, it is usually about 1 to about 10 hours and preferably about 2 to about 5 hours. Whether the dehydration reaction has terminated can be determined by reference to, for example, whether the generation of by-product water is occurring. Although the isomerization reaction proceeds at ordinary pressures, it may be carried out under pressure or under reduced pressure as necessary.

The isomerization reaction is preferably carried out in the presence of an acid catalyst. The isomerization reaction from 2,4'-BS to 4,4'-BS takes place simultaneously with the dehydration reaction, and therefore while an acid catalyst may be introduced into the reaction system at the same time as the components of the dehydration reaction, it may be introduced into the reaction system during or after the dehydration reaction.

Phenolsulfonic acid functions as an acid catalyst as well. Therefore, when phenolsulfonic acid is used as a reaction component or when phenolsulfonic acid is generated as a reaction intermediate, replenishing amounts of acid catalyst may be added as necessary, or an acid catalyst that has a stronger catalytic effect than phenolsulfonic acid may be used. Acid catalysts that have a stronger catalytic effect than phenolsulfonic acid are, for example, those that are described below as preferable acid catalysts.

Examples of acid catalysts are aromatic sulfonic acids such as benzenesulfonic acid, chlorobenzenesulfonic acid, benzene-1,3-disulfonic acid, chlorobenzene-2,4-disulfonic acid, bromobenzene-2,4-disulfonic acid, fluorobenzene-2,4-disulfonic acid, toluene-2,4-disulfonic acid, ethylbenzene-2,4-disulfonic acid, benzene-1,3,5-trisulfonic acid, chlorobenzene-2,4,6-trisulfonic acid, bromobenzene-2,4,6-trisulfonic acid, fluorobenzene-2,4,6-trisulfonic acid, toluene-2,4,6-trisulfonic acid and ethylbenzene-2,4,6-trisulfonic acid; aliphatic sulfonic acids such as trifluoromethanesulfonic acid; resins having a sulfo group, such as perfluorinated ionomers (e.g., trade name: Nafion); etc. Preferable among such examples are benzene-1,3-disulfonic acid, chlorobenzene-2,4-disulfonic acid, bromobenzene-2,4-disulfonic acid, fluorobenzene-2,4-disulfonic acid, toluene-2,4-disulfonic acid, ethylbenzene-2,4-disulfonic acid, benzene-1,3,5-trisulfonic acid, chlorobenzene-2,4,6-trisulfonic acid, bromobenzene-2,4,6-trisulfonic acid, fluorobenzene-2,4,6-trisulfonic acid, toluene-2,4,6-trisulfonic acid and ethylbenzene-2,4,6-trisulfonic acid. Acid catalysts may be used singly or as a combination of two or more species.

The amount of acid catalyst is not limited insofar as it is a catalytic amount, and can be selected from a broad range. It is usually about 0.5 to about 10 mol %, and preferably about 2 to about 5 mol %, based on the sulfonating agent.

The reaction suspension produced in the dehydration reaction is mixed with a polar solvent to at least partially dissolve the dihydroxydiphenylsulfone thus generated. When mixed with a polar solvent, impurities such as 2,4'-BS, phenolsulfonic acid and the like are dissolved in the liquid phase, thereby enabling the desired 4,4'-BS of high purity to be obtained. The manner of mixing a polar solvent with the reaction suspension is not limited. A polar solvent may be added to the reaction suspension, and the reaction suspension may be added to a polar solvent.

In case the isomerization reaction has been carried out as necessary, the reaction suspension after the isomerization reaction is mixed with a polar solvent to at least partially dissolve the resulting dihydroxydiphenylsulfone. Although the amount of BS to be dissolved is not limited insofar as the effect of the invention can be attained, the more BS dissolved, the more likely 4,4'-BS of higher purity obtained, and it is therefore most preferable to completely dissolve the suspended BS. For example, when 4,4'-BS with a purity of 99.5% or greater is desired, it is preferable to completely dissolve the suspended BS.

Examples of usable polar solvents are $C_{4-15}$ higher alcohols, polyols, and phenols. Examples of higher alcohols are butanol, amyl alcohol, octyl alcohol, etc. Examples of polyols are ethylene glycol, diethylene glycol, ethylene glycol monoethyl ether (e.g., trade name: Ethylcellosolve), ethylene glycol monobutyl ether (e.g., trade name: Butylcellosolve), etc. Examples of phenols are phenol, cresol, xylenol, etc. Polar solvents can be used singly or as a combination of two or more species. Phenol is particularly preferable as a polar solvent. The combination of phenol and mesitylene is preferably as the combination of polar solvent and nonpolar solvent.

Although the proportion of polar solvent is not limited insofar as the desired amount of BS can be dissolved, it is usually about 10 wt. % or greater, and preferably about 30 to about 70 wt. %, of the total weight of reaction medium and polar solvent. When aromatic nonpolar solvents are used in combination with other nonpolar solvents such as aliphatic hydrocarbon solvents, the total weight of aromatic nonpolar solvents and other nonpolar solvents is regarded as the weight of reaction medium.

BS dissolves without heating, but may be heated as necessary. Although the heating temperature is not limited insofar as the BS produced in the reaction can be at least partially dissolved, it is usually at least about 130° C., preferably about 150 to about 220° C., and more preferably about 160 to about 200° C.

BS dissolves at ordinary pressures, but may be dissolved under pressure as necessary. A pressure of about 0.01 to about 1 MPa, and preferably about 0.05 to about 0.5 MPa, is usually applied. Pressure application enables the amount of polar solvent such as phenol to be reduced, resulting in enhanced yields.

4,4'-BS is then precipitated. This process is sometimes referred to as the primary precipitation, and crystals obtained by the primary precipitation are sometimes referred to as the "primary crystals".

Although the precipitation temperature is not limited insofar as 4,4'-BS precipitates, it is usually about 150° C. or lower, preferably about 100° C. or lower, and more preferably about 60° C. or lower. The difference between heating temperature and precipitation temperature is usually at least about 20° C., preferably at least about 50° C., and more preferably about 50 to about 150° C.

The primary precipitation gives 4,4'-BS of high purity. The purity of the 4,4'-BS thus obtained is usually about 98% or greater, and it is about 99% or greater in preferable conditions and about 99.5% or greater in more preferable conditions. Precipitated 4,4'-BS of high purity can be isolated and recovered according to a known solid-liquid separation technique such as filtration or decantation. 4,4'-BS may be dried after isolation and recovery if necessary.

Optionally, in the present invention, primarily precipitated 4,4'-BS is isolated by a known solid-liquid separation techniques such as filtration or decantation, the solvent contained in the 4,4'-BS-separated fluid is distilled to make the fluid a suspension or distillation residue, and solids contained in the suspension or the residue is at least partially dissolved in a mixed solvent of a polar solvent and an aromatic nonpolar solvent to precipitate 4,4'-BS (secondary precipitation). Crystals obtained by the secondary precipitation are sometimes referred to as the "secondary crystals". 4,4'-BS precipitated by secondary precipitation can be isolated by filtration or decantation.

Heat may be applied as necessary when the solvents are distilled off. Although the heating temperature is not limited insofar as distillation progresses, it is preferably about 120° C. or higher, and more preferably about 140 to about 175° C. Heating temperatures with the ranges above enhance the isomerization reaction from 2,4'-BS to 4,4'-BS, thereby enabling 4,4'-BS of higher purity to be produced as secondary crystals. Although the distillation of the solvents can be carried out at ordinary pressures, it may be carried out under pressure or under reduced pressure as necessary.

The temperature after solvent distillation may be maintained at the isomerization temperature or higher if necessary. Maintaining the temperature at the isomerization temperature or higher enhances the isomerization reaction from 2,4'-BS to 4,4'-BS. Although the temperature level to be maintained is not limited insofar as the isomerization reaction from 2,4'-BS to 4,4'-BS progresses, it is usually about 120° C. or higher, and preferably about 140° C. to about 175° C. Temperatures within the ranges given above allow a prompt isomerization reaction. Although the duration of maintaining the temperature at the isomerization temperature or higher can be suitably selected according to the reaction temperature and other factors, it is usually about 1 to about 10 hours and preferably about 2 to about 5 hours. Although the isomerization reaction proceeds at ordinary pressures, it can be carried out under pressure or under reduced pressure as necessary.

The solvents recovered by distillation or a like method can be recycled for the dehydration reaction. When a solvent other than phenol is used as a polar solvent, it is removed according to known methods such as distillation, and the rest is reused as a solvent for the dehydration reaction. When phenol is used as a polar solvent, removal thereof is unnecessary. When the solvents are recycled for the dehydration reaction, replenishing amounts of phenol, sulfonating agent, phenolsulfonic acid, acid catalyst, etc., are added as necessary.

Thereafter, the solids contained in the suspension or the residue is at least partially dissolved in a mixed solvent of a polar solvent and an aromatic nonpolar solvent. The more the solids or residue is dissolved, the more likely secondary crystals of higher purity will be obtained. It is therefore most preferable to completely dissolve the solids and residue.

Aromatic nonpolar solvents can be used in combination with other nonpolar solvents such as aliphatic hydrocarbon solvents also for the secondary precipitation. When used in combination with other nonpolar solvents, aromatic nonpolar solvents are used usually in a proportion of about 50 wt. % or greater, and preferably about 70 wt. % or greater, of the entire nonpolar solvents.

Although the ratio of polar solvent to aromatic nonpolar solvent contained in the mixed solvent is not limited, the proportion of polar solvent is about 10 to about 90 wt. %, and preferably about 30 to about 70 wt. %, of the entire mixed solvent. When phenol is used as an aromatic nonpolar solvent, the ratio of phenol to aromatic nonpolar solvent is preferably about the same as that described with respect to the dehydration reaction.

The amount of mixed solvent is not limited insofar as the desired amount of BS, or residue, can be dissolved. The weight ratio of mixed solvent to BS or residue is usually about 1 to 1-10, and preferably about 1 to 2-5.

After dissolution, the procedure for 4,4'-BS precipitation is repeated (secondary precipitation). Although the precipitation temperature is not limited insofar as 4,4'-BS precipitates, it is usually about 150° C. or lower, preferably about 100° C. or lower, and more preferably about 60° C. or lower. The difference between heating temperature and precipitation temperature is usually at least about 20° C., preferably at least about 50° C., and more preferably about 50 to about 150° C.

Secondary crystals may be isolated and recovered according to known solid-liquid separation techniques such as filtration and decantation. Secondary crystals may be dried after isolation and recovery if necessary.

Although the secondary crystals thus recovered are of high purity as is, they can be introduced for recrystallization into the reaction system of another dehydration reaction between phenol and a sulfonating agent or phenolsulfonic acid before or after the dehydration reaction. When secondary crystals are introduced into the reaction system after a dehydration reaction, they may be added at any time before or after mixing the reaction suspension with a polar solvent. When the isomerization reaction is carried out subsequent to a dehydration reaction, secondary crystals are added at any time before or after the isomerization reaction. In this case also, secondary crystals can be added at any time before or after mixing the reaction suspension with a polar solvent. The obtainment of secondary crystals as described above can enhance the yield of 4,4'-BS.

The liquid obtained from the isolation and recovery of secondary crystals can be recycled as a solvent for the dehydration reaction. When a solvent other than phenol is used as a polar solvent, it is removed according to a known method such as distillation, and rest of the liquid is reused as a solvent for the dehydration reaction. When phenol is used as a polar solvent, although the removal thereof is not necessary, it is preferable to purify the liquid by distillation for reuse. When the liquid is recycled as a solvent for the dehydration reaction, replenishing amounts of phenol, sulfonating agent, phenolsulfonic acid, acid catalyst, etc., are added as necessary.

Primary crystals and secondary crystals may be further purified as necessary. Moreover, primary crystals and secondary crystals can be combined. An example is mixing primary crystals with a solvent such as water, alcohol (e.g, methanol or ethanol) or the like; activated carbon; a reducing agent such as a hydrosulfite; ethylenediaminetetraacetic acid (EDTA); and the like to dissolve the primary crystals, then removing the activated carbon by filtration or like method, and precipitating 4,4'-BS from the resulting liquid.

According to the present invention, 4,4'-BS of very high purity can be produced (for example, 98% or greater, 99% or greater in preferable conditions, and 99.5% or greater in more preferable conditions).

According to the present invention, 4,4'-BS can be produced in high yields. By way of secondary crystals, 4,4'-BS can be produced in higher yields.

According to the present invention, 4,4'-BS of high purity can be produced through simple steps without complicated procedures.

The process of the present invention can produce 4,4'-BS as primary crystals containing substantially no by-product phenolsulfonic acid or trihydroxytriphenyldisulfone (TTDS).

Moreover, the present invention provides a production process that discharges very little or no waste water and waste materials, i.e., provides a closed system, when the solvent is recovered from the liquid after the removal of primary crystals or secondary crystals and recycled as a solvent for the dehydration reaction (especially when phenol is used as a polar solvent).

BEST MODE FOR CARRYING OUT THE INVENTION

Examples and a comparative example are given below to illustrate the invention in more detail, but the scope of the invention is not limited to these examples.

EXAMPLE 1

One hundred grams (1.0 mol) of 98% sulfuric acid was added dropwise to a mixture of 144 g of mesitylene and 189 g (2.0 mol) of phenol while stirring. The reaction solution was heated in a 200° C. oil bath for dehydration. The reaction solution started boiling at a temperature near 145° C. Distillates were condensed by a condenser and separated into 2 phases by a trap. The upper phase, i.e., the organic phase, was continuously returned to the reaction system. Five hours after the beginning of distillation, the temperature of the reaction solution was 165° C., and the amount of water in the lower phase separated by the trap was steady at 38 ml. Crystals were precipitated in the reaction system, thereby forming a slurry. A small amount of the resulting reaction suspension was sampled and analyzed by HPLC. The result showed a composition (weight ratio) of 4,4'-BS/2,4'-BS/ trihydroxytriphenyldisulfone=92.5/6.0/1.5.

Phenol in an amount of 189 g was added to the reaction suspension and heated hermetically. When the temperature reached 185° C., the crystals were completely dissolved. The pressure in the reaction system at this point was 0.07 MPa.

The solution was then cooled while stirring. Crystals started precipitating at 165° C. The solution was further cooled to 40° C., and the precipitated crystals were filtered off, washed and dried, thereby giving 208 g of crystals. The crystals thus obtained had a composition (weight ratio) of 4,4'-BS/2,4'-BS/trihydroxytriphenyldisulfone=99.5/0.5/0. The yield of 4,4'-BS based on the starting sulfuric acid was 83%. Phenolsulfonic acid and like sulfonic acids were not detected in the crystals.

EXAMPLE 2

A dehydration reaction was carried out in the same manner as in Example 1. After the reaction, 189 g of phenol was added to the reaction suspension. The mixture was heated to about 180° C. Although most crystals were dissolved, some crystals were present as a suspension (slurry), and then precipitation by cooling and aftertreatment were conducted in the same manner as in Example 1, thereby giving 208 g of crystals. The crystals thus obtained had a composition (weight ratio) of 4,4'-BS/2,4'-BS/trihydroxytriphenyldisulfone=99.2/0.8/0. The yield of 4,4'-BS based on the starting sulfuric acid was 83%. Phenolsulfonic acid and like sulfonic acids were not detected in the crystals.

EXAMPLE 3

The filtrate after filtering off the primary crystals of Example 1 (4,4'-BS/2,4'-BS=48:52 in the filtrate) was heated to 165° C. The solvents contained therein were recovered by distillation under reduced pressure until the solvent distillation terminated. The temperature was maintained at 170° C. for 2 hours to substantially complete the isomerization reaction from 2,4'-BS to 4,4'-BS, thereby giving a distillation residue.

This distillation residue was mixed with 48 g of phenol and 36 g of mesitylene, and the mixture was heated for complete dissolution and then cooled to 40° C., thereby precipitating crystals. The crystals thus obtained were filtered off, washed and dried, thereby giving 28 g of secondary crystals. These secondary crystals had a composition (weight ratio) of 4,4'-BS/2,4'-BS/trihydroxytriphenyldisulfone=99.1/0.6/0.3. The yield of 4,4'-BS based on the starting sulfuric acid in Example 1 was 11%.

The procedures described in Example 1 were repeated except that all of the secondary crystals obtained above were introduced into the reaction system after the dehydration reaction, thereby giving 237 g of crystals. The crystals thus obtained had a composition (weight ratio) of 4,4'-BS/2,4'-BS/trihydroxytriphenyldisulfone=99.5/0.5/0. The yield of 4,4'-BS based on the starting sulfuric acid was 94%.

Phenolsulfonic acid and like sulfonic acids were not detected in the crystals.

EXAMPLE 4

One hundred grams (1.0 mol) of 98% sulfuric acid was added dropwise to a mixture of 144 g of mesitylene, 189 g (2.0 mol) of phenol and 11.9 g (0.05 mol) of benzene-1,3-disulfonic acid while stirring. The reaction solution was heated in a 200° C. oil bath. The reaction solution started boiling at a temperature near 145° C. Distillates were condensed by a condenser and separated into 2 phases by a trap. The upper phase, i.e., the organic phase, was continuously returned to the reaction system. Five hours after the beginning of distillation, the temperature of the reaction solution was 165° C., and the amount of water in the lower phase separated by the trap was steady at 38 ml. Crystals were precipitated in the reaction system, thereby forming a slurry. A small amount of the reaction slurry was sampled and analyzed by HPLC. The result showed a composition (weight ratio) of 4,4'-BS/2,4'-BS/trihydroxytriphenyldisulfone=96.0/3.0/1.0.

Thereafter, aftertreatment was conducted in the same manner as in Example 1, thereby giving 237 g of crystals. The crystals thus obtained had a composition (weight ratio) of 4,4'-BS/2,4'-BS/trihydroxytriphenyldisulfone=99.5/0.5/0. The yield of 4,4'-BS based on the starting sulfuric acid was 94%.

Sulfonic acids, chiefly benzene-1,3-disulfonic acid and phenolsulfonic acid, were not detected in the crystals.

EXAMPLE 5

A dehydration reaction was carried out in the same manner as in Example 1 except for using 208 g of 3,4-dichlorotoluene in place of mesitylene, thereby giving a reaction suspension. A small amount of the reaction suspension was sampled and analyzed by HPLC. The result showed a composition (weight ratio) of 4,4'-BS/2,4'-BS/trihydroxytriphenyldisulfone=91.5/7.0/1.5.

Crystals present in the reaction suspension were completely dissolved in the same manner as in Example 1. The solution was then cooled, thereby giving 203 g of crystals. The crystals thus obtained had a composition (weight ratio) of 4,4'-BS/2,4'-BS/trihydroxytriphenyldisulfone=99.3/0.7/0. The yield of 4,4'-BS based on the starting sulfuric acid was 81%. Phenolsulfonic acid and like sulfonic acids were not detected in the crystals.

EXAMPLE 6

A dehydration reaction was carried out in the same manner as in Example 1 except for using 240 g of 1,2,4-trichlorobenzene in place of mesitylene, thereby giving a reaction suspension. A small amount of the reaction suspension was sampled and analyzed by HPLC. The result showed a composition (weight ratio) of 4,4'-BS/2,4'-BS/trihydroxytriphenyldisulfone=90.7/7.6/1.7.

Crystals present in the reaction suspension were completely dissolved in the same manner as in Example 1 except that, instead of phenol, 190 g of cresol was added to the reaction suspension. The solution was then cooled, thereby giving 200 g of crystals. The crystals thus obtained had a composition (weight ratio) of 4,4'-BS/2,4'-BS/trihydroxytriphenyldisulfone=99.4/0.6/0. The yield of 4,4'-BS based on the starting sulfuric acid was 80%. Phenolsulfonic acid and like sulfonic acids were not detected from the crystals.

COMPARATIVE EXAMPLE 1

A dehydration reaction was carried out in the same manner as in Example 1. The reaction suspension without any addition of phenol was cooled to 40° C., and the precipitated crystals were filtered off, washed and dried, thereby giving 245 g of crystals. The crystals had a 4,4'-BS/2,4'-BS/trihydroxytriphenyldisulfone composition (weight ratio) of 92.5/6.0/1.5. The crystals also contained sulfonic acids, chiefly phenolsulfonic acid, in a proportion of 2%. The yield of 4,4'-BS based on the starting sulfuric acid was 89%.

The invention claimed is:

1. A process for producing 4,4'-dihydroxydiphenylsulfone of high purity comprising the steps of:
    subjecting phenol in combination with a sulfonating agent or phenolsulfonic acid to a dehydration reaction in the presence of mesitylene while suspending the resulting dihydroxydiphenylsulfone therein;
    mixing the resulting reaction suspension with phenol to at least partially dissolve the dihydroxydiphenylsulfone; and
    precipitating dissolved 4,4'-dihydroxydiphenylsulfone.

2. A process for producing 4,4'-dihydroxydiphenylsulfone of high purity comprising the steps of:
    subjecting phenol in combination with a sulfonating agent or phenolsulfonic acid to a dehydration reaction in the presence of mesitylene while suspending the resulting dihydroxydiphenylsulfone therein;
    mixing the resulting reaction suspension with phenol to at least partially dissolve the dihydroxydiphenylsulfone;
    primarily precipitating dissolved 4,4'-dihydroxydiphenylsulfone;
    isolating the resulting 4,4'-dihydroxydiphenylsulfone by filtration or decantation;
    distilling off the solvents contained in the liquid obtained after the isolation of the 4,4'-dihydroxydiphenylsulfone to produce a suspension or distillation residue;
    at least partially dissolving solids contained in the suspension or the residue in a mixed solvent of a polar solvent and a nonpolar solvent; and
    secondarily precipitating 4,4'-dihydroxydiphenylsulfone.

3. A process for producing 4,4'-dihydroxydiphenylsulfone of high purity according to claim 1, wherein the dehydration reaction between phenol and a sulfonating agent or phenolsulfonic acid is carried out in the presence of an acid catalyst.

4. A process for producing 4,4'-dihydroxydiphenylsulfone of high purity according to claim 1, wherein the reaction suspension and the phenol are mixed while heating under pressure to at least partially dissolve dihydroxydiphenylsulfone.

5. A process for producing 4,4'-dihydroxydiphenylsulfone of high purity according to claim 2, wherein the solids contained in the suspension or the residue is at least partially dissolved in a mixed solvent of phenol and mesitylene while heating under pressure.

6. A process for producing 4,4'-dihydroxydiphenylsulfone of high purity according to claim 2, wherein before or after the dehydration reaction between phenol and a sulfonating agent or phenolsulfonic acid, 4,4'-dihydroxydiphenylsulfone obtained by secondary precipitation is introduced into the reaction system.

7. A process for producing 4,4'-dihydroxydiphenylsulfone of high purity according to claim 2, wherein the temperature is maintained at the isomerization temperature or higher even after phenol and mesitylene contained in the liquid obtained after the isolation of the primarily precipitated 4,4'-dihydroxydiphenylsulfone by filtration or decantation are distilled off to produce a suspension or distillation residue.

8. A process for producing 4,4'-dihydroxydiphenylsulfone of high purity according to claim 2, wherein the dehydration reaction between phenol and a sulfonating agent or phenolsulfonic acid is carried out in the presence of an acid catalyst.

9. A process for producing 4,4'-dihydroxydiphenylsulfone of high purity according to claim 2, wherein the reaction suspension and the phenol are mixed while heating under pressure to at least partially dissolve dihydroxydiphenylsulfone.

10. A method of producing 4,4'-dihydroxydiphenylsulfone comprising:
    subjecting phenol in combination with a sulfonating agent or phenolsulfonic acid to a dehydration reaction in the presence of mesitylene while suspending therein the generating dihydroxydiphenylsulfone, which is a isomeric mixture of 4,4'-dihydroxydiphenylsulfone and 2,4'-dihydroxydiphenylsulfone, at an isomerization temperature or higher;
    mixing the resulting reaction suspension with phenol to at least partially dissolve the dihydroxydiphenylsulfone; and
    precipitating dissolved 4,4'-dihydroxydiphenylsulfone at a precipitation temperature.

11. The method according to claim 10, wherein while suspending the generating dihydroxydiphenylsulfone in mesitylene, an isomerization reaction is carried out in the presence of an acid catalyst.

12. The method according to claim 10, further comprising:
    isolating the precipitated 4,4'-dihydroxydiphenylsulfone by filtration or decantation in a solvent;
    distilling off the solvent after the isolation of the 4,4'-dihydroxydiphenylsulfone to produce a suspension or distillation residue;
    at least partially dissolving solids contained in the suspension or the residue in a mixed solvent of phenol and mesitylene; and
    secondarily precipitating 4,4'-dihydroxydiphenylsulfone.

13. The method according to claim 12, further comprising isolating the secondarily precipitated 4,4'-dihydroxydiphenylsulfone by filtration or decantation at a purity of 99% or higher.

* * * * *